United States Patent [19]

Daniels

[11] 4,393,224

[45] Jul. 12, 1983

[54] TELOMERIZATION OF BUTADIENE AND CARBON DIOXIDE

[75] Inventor: James A. Daniels, Frodsham, England

[73] Assignee: Imperial Chemical Industries Plc., London, England

[21] Appl. No.: 312,914

[22] Filed: Oct. 19, 1981

[30] Foreign Application Priority Data

Oct. 20, 1980 [GB] United Kingdom ................ 8033740

[51] Int. Cl.$^3$ ........................................... C07D 309/32
[52] U.S. Cl. .................................. 549/273; 560/208; 560/225
[58] Field of Search ......................................... 549/273

[56] References Cited

U.S. PATENT DOCUMENTS 4,167,513 9/1979 Musco et al. .................... 260/343.5

OTHER PUBLICATIONS

Musco, J. C. S., Perkin I, 1980, p. 693.
Sasaki et al., J. C. S. Chem. Comm., 1976, p. 605.
Musco et al., Chem. Abs. 89:128999n.
Inoue et al., Chem. Abs. 89:196885x.

Primary Examiner—Jane T. Fan
Attorney, Agent, or Firm—Cushman, Darby & Cushman

[57] ABSTRACT

A process for the manufacture of 2-ethylidenehept-6-en-5-olide which comprises reacting in a liquid medium 1,3-butadiene with carbon dioxide in the presence of a palladium complex catalyst and a tertiary amine.

12 Claims, No Drawings

TELOMERIZATION OF BUTADIENE AND CARBON DIOXIDE

The present invention relates to a process for the telomerization of butadiene and carbon dioxide, and especially to a process for the selective production of a lactone.

Inoue et al., Chem Comm. 1976, 65 describes a process in which butadiene is reacted with carbon dioxide in a polar aprotic solvent in the presence of certain palladium-phosphine complexes (e.g. Pd(Ph$_2$PCH$_2$CH$_2$PPh$_2$)$_2$) to give a five membered lactone, 2-ethylidene-hept-5-en-4-olide, in small yields (0.4 to 12.3% yield based on butadiene), together with much higher yields of butadiene oligomers (60–85% yield).

Musco, J. Chem. Soc. Perkin I, 1980, 693 describes the use of palladium complexes of unidentate tertiary phosphine ligands (of the type [Pd L$_n$]) to catalyse the co-oligomerisation of butadiene and carbon dioxide in non-polar solvents (e.g. benzene) to yield mixtures of δ-lactones (e.g. (E)-2-ethylidenehept-6-en-5-olide), octadienyl esters (e.g. octadienyl esters of (E)-2-ethylidenehepta-4,6-dienoic acid), and octatrienes (e.g. octa-1,3,7-triene). The distribution of reaction products depended on the ligand bound to the palladium, but P(C$_6$H$_{11}$)$_3$ and PPr$_3^i$ gave the best yields of the δ-lactone (45% and 35% yield of δ-lactone at conversions of butadiene of 62% and 78% respectively). Appreciable quantities of octatrienes were produced.

German DOS No. 2838610 describes a process for the production of octadienyl esters of 2-ethylidenehepta-3,5-diene and 2-vinylhepta-3,5-diene acid with the general formula C$_8$H$_{11}$COOC$_8$H$_{13}$ and isomers thereof and an unsaturated δ-lactone, 2-ethylidenehept-6-en-5-olide, which process comprises reacting 1,3-butadiene with carbon dioxide in an inert atmosphere, in the presence of palladium/phosphorus complexes Pd[P(R)$_3$]$_x$, in which x is a whole number between 2 and 4 and R which may be substituted, each R being the same or different, is an alkyl radical or a cycloalkyl radical with up to 8 carbon atoms or a phenyl radical. The process is suitably carried out in the presence of a solvent, and effective palladium/phosphine complexes as catalysts include Pd(PEt$_3$)$_x$, Pd(PBu$_3$)$_x$, Pd(PCy$_3$)$_x$, and Pd(PPh$_3$)$_x$. To obtain the lactone as the main product, an overall pressure in the range 250 to 300 bar is recommended and the preferred temperature is 60° to 85° C. Conversions and selectivities are not quoted but the Examples indicate that considerable quantities of non-carboxylated octatrienes are formed.

Ito et al. (Nippon Kagaku Kaishi, 1979, 1276) describes the reaction of butadiene and carbon dioxide in dimethylformamide as solvent in the presence of a palladium complex catalyst e.g. Pd(Ph$_3$)$_4$ and sodium phenate as a co-catalyst. Only low yields (0–7%) of lactones were obtained as compared with the much higher yields of octadienoic acids (22–69%) and of octatrienes (plus phenoxyoctatriene, the reaction product of octatrienes and sodium phenate) which totalled 31–78%.

Lactones are useful monomers for the synthesis of polyester resins and can also be used as intermediates in the synthesis of fungicides, pesticides and plasticisers. In the aforesaid prior art processes, the lactone products are admixed with appreciable quantities of either the non-carboxylated octatrienes or carboxylated esters. The valuable butadiene is thus being wasted in the production of materials of little value whilst the desired lactone is formed only in poor selectivity.

It has now been found that carbon dioxide can be reacted with butadiene much more efficiently than has previously been disclosed to produce the desired lactone in high selectivity if the reaction is performed in the presence of a palladium complex catalyst and a tertiary amine.

Thus, according to the present invention, there is provided a process for the manufacture of 2-ethylidenehept-6-en-5-olide which comprises reacting in a liquid medium 1,3-butadiene with carbon dioxide in the presence of a palladium complex catalyst and a tertiary amine.

The palladium complex catalyst preferably comprises a complex of palladium with either a phosphorus (III) compound or pyridine or a substituted pyridine.

The complexes of palladium typically contain phosphine (PR$_3^1$), phosphinite [PR$_2^1$(OR$^2$)], phosphonite [PR$^1$(OR$^2$)$_2$] and phosphite P(OR$^1$)$_3$ ligands in which R$^1$ and R$^2$, which may be the same or different, are alkyl or cycloalkyl groups, preferably containing up to 8 carbon atoms, e.g. methyl, ethyl etc. or an aryl group e.g. phenyl. The aforesaid phosphorus containing ligands may optionally be associated with one or more ligands L each containing one or more unsaturated double bonds which are capable of co-ordinating with the palladium atom. Typical ligands L include olefins and aliphatic or aromatic anhydrides and ketones. Preferably the ligand L when present is a quinone e.g. benzoquinone or naphthoquinone. Preferred palladium complexes include the phosphine complexes [Pd(PR$_3^1$)$_3$L] where R$^1$ and L are as hereinbefore defined. Especially preferred complexes include [Pd(PPH$_3$)$_4$], [Pd(PPh$_3$)$_2$(p-benzoquinone)], [Pd(PPh$_3$)$_2$(naphthoquinone)] and [Pd{P(OMe)$_2$Ph}$_2$(p-benzoquinone)]. Typical complexes of palladium and pyridine or a substituted pyridine include [Pd(pyridine)(p-benzoquinone)] and [Pd(pyridine)(dibenzylideneacetone)]. Methods for the preparation of such complexes are known.

The palladium complex is suitably used in an amount of 0.1 to 20 mmol, preferably 0.2 to 5 mmol per mole of butadiene.

The tertiary amine used in the process of the invention is a compound R$_3$N wherein the R substituents may be the same or different, each being a hydrocarbyl group or two of the R substituents taken together with the nitrogen atom from a saturated heterocyclic radical. Amines having a pKa value in the range 10 to 14 are preferred. Examples of such tertiary amines include aliphatic tertiary amines such as triethylamine and alkyl substituted piperidines such as N-ethylpiperidine.

The tertiary amine is suitably used in an amount of 10 to 100 mmol, preferably 15 to 50 mmol, per mole of butadiene.

The process of the invention provides 2-ethylidenehept-6-en-5-olide in much higher selectivity than prior art processes. The additional benefit of a significantly increased reaction rate, may be achieved by also including in the reaction mixture a quinone or a hydroquinone or a mixture thereof. The higher reaction rate permits shorter reaction times and the use of much lower pressures than are used in prior art processes.

Suitable quinones and hydroquinones include compounds of the formulae:

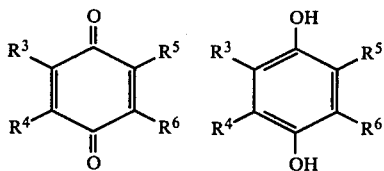

wherein each of $R^3$, $R^4$, $R^5$ and $R^6$, independently, represents hydrogen or a hydrocarbon radical or $R^3$ and $R^4$ taken together and/or $R^5$ and $R^6$ taken together form part or parts of a fused cyclic ring system. Examples of suitable quinones include p-benzoquinone and 1,4-naphthoquinone. Examples of suitable hydroquinones include hydroquinone itself (i.e. p-dihydroxybenzene).

The quinone and/or hydroquinone is suitably used in an amount of 1 to 25 mmol, preferably 2 to 10 mmol per mole of butadiene.

It is also advantageous if the reaction mixture contains other components of the palladium complexes additional to those initially present in the complex. Thus, the reaction is assisted by including a phosphorus (III) compound, for example triphenylphosphine, in the reaction mixture. Amounts of 0.5 to 10 mmol per mole of butadiene are effective. Pyridine and substituted pyridines have a similar advantageous effect.

The process of the invention is preferably carried out under substantially anhydrous conditions. Small amounts of water, for example up to 12.5 mmole per mole of butadiene, are not harmful and, in fact, the reaction rate can be increased by the inclusion of water in the reaction mixture. Amounts of water above this level, however, reduce the lactone selectivity and increase the formation of octatrienes.

The process is conveniently carried out in the presence of a polar aprotic solvent, for example acetonitrile. Suitable reaction temperatures are in the range 20°–100° C., preferably 40°–80° C. The overall pressure is usually in the range 10 to 100 bar, preferably 10 to 50 bar. Reaction times of 6 to 18 hours are typical. Since the process produces only small yields of by-products, very little butadiene is lost and any unreacted butadiene can easily be recovered from the final reaction mixture for use in subsequent reactions.

The invention is illustrated but not limited by the following Examples in which the lactone (I) and ester (II) products have the following structures:

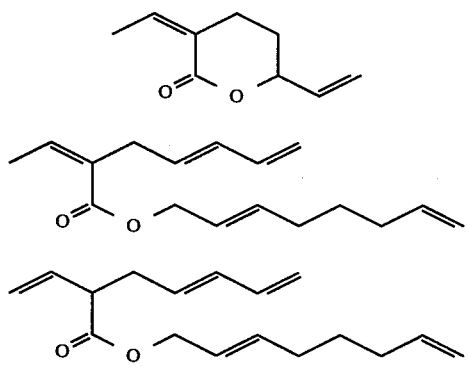

EXAMPLE 1

20 ml of acetonitrile, 0.1 g (0.14 mmol) of [Pd(PPh$_3$)$_2$(p-benzoquinone)], 0.072 g (0.27 mmol) of triphenylphosphine, 0.5 ml (3.6 mmol) of N-ethylpiperidine, 0.08 g (0.73 mmol) of hydroquinone and 11.5 g (0.21 mol) of butadiene were reacted for 18 hours at 60° C. under 30 bar of $CO_2$ pressure in a stirred autoclave of 100 ml capacity. The mixture was cooled to room temperature and the solvent removed on a rotary evaporator with water pump vacuum at 60° C. to leave a pale-yellow oil.

The oil was separated into three main fractions by high pressure liquid chromatography on silica using n-hexane and ethyl acetate as eluents. Infra-red, nuclear magnetic resonance and mass spectroscopy techniques confirmed the three fractions to consist of octatrienes (mainly the 1,3,7-isomer), lactone(I) and esters(II). A gas chromatography column (10% Dexil on Chromosorb W(HP)) at 140° C. was standardised for these products and the ratio of one to the others determined.

The butadiene conversion was found to be 76% and product selectivities were 89% lactone (I), 4% esters (II) and 5% octatrienes, the yield of lactone being 525 mol per mol of palladium metal (averaging 29 mol per hour).

In the absence of N-ethylpiperidine, the following results were typical; butadiene conversion 22% and product selectivities of 69% lactone (I), 6% esters (II) and 20% octatrienes, the yield of lactone being 112 mol per mol of palladium metal (averaging 6.2 mol per hour).

In the absence of the hydroquinone (but in the presence of the base), the butadiene conversion was 23% and product selectivities of 88% lactone(I), 5% esters-(II) and 6% octatrienes, the yield of lactone being 153 mol per mol of palladium (averaging 8.5 mol per hour).

EXAMPLE 2

20 ml of acetonitrile 0.1 g (0.14 mmol) of [Pd(PPh$_3$)$_2$(p-benzoquinone)], 0.072 g (0.27 mmol) of triphenylphosphine, 0.5 (4 mmol) of N-ethylpiperidine, 0.08 g (0.73 mmol) of p-benzoquinone and 11.5 g (0.21 mmol) of butadiene were reacted for 18 hours at 60° C. under 45 bar of $CO_2$ pressure as described in Example 1. The butadiene conversion was found to be 58%, the product selectivities were 89% lactone (I), 4% esters (II) and 6% octatrienes, the yield of lactone being 385 mol. per mole of palladium metal (averaging 21 mol per hour).

EXAMPLE 3

20 ml of acetonitrile, 0.1 g (0.14 mmol) of [Pd(PPh$_3$)$_2$(p-benzoquinone)], 0.072 g (0.27 mmol) of triphenylphosphine, 0.5 ml (4 mmol) of N-ethylpiperidine, 0.08 g (0.73 mmol) of hydroquinone, 0.04 g (0.36 mmol) of p-benzoquinone and 11.5 g (0.21 mol) of butadiene were reacted for 18 hours at 60° C. under 30 bar of $CO_2$ as described in Example 1. The butadiene conversion was found to be 88%, the product selectivities were 92% lactone (I), 4% esters (II) and 3% octatrienes, the yield of lactone being 621 mol per mol of palladium metal (averaging 34.5 mol per hour).

EXAMPLE 4

The reaction was carried out following the procedure described in Example 3 with the $CO_2$ pressure at 13.5 bar and the reaction time 3 hours. The butadiene conversion was found to be 56%, the product selectivities were 91% lactone (I), 3% esters (II) and 5% octatrienes, the yield of lactone being 392 mol per mol of palladium metal (averaging 130 mol per hour).

EXAMPLE 5

The reaction was carried out following the procedure described in Example 3 with the $CO_2$ pressure at 13.5 bar, the time of reaction 4 hours and 0.2 g (0.28 mmol) of [Pd(PPh$_3$)$_2$(p-benzoquinone)] and 0.14 g (0.54 mmol) of triphenylphosphine. The butadiene conversion was found to be 72%, the product selectivities were 90% of lactone (I) 3% esters (II) and 6% octatrienes, the yield of lactone being 250 mol per mol of palladium metal (averaging 62.5 mol per hour).

EXAMPLE 6

The reaction was carried out following the procedure described in Example 1 with no triphenylphosphine added. The butadiene conversion was found to be 50.5%, the product selectivities were 87% lactone (I), 3% esters and 9% octatrienes, the yield of lactone being 326 mol per mol of palladium metal (averaging 18 mol per hour).

EXAMPLE 7

The reaction was carried out following the procedure described in Example 1 with 0.36 g (1.36 mmol) of triphenylphosphine added. The butadiene conversion was found to be 78%, the product selectivities were 73% lactone (I), 13% esters (II) and 9% octatrienes, the yield of lactone being 435 mol per mol of palladium metal (averaging 24 mol per hour).

EXAMPLE 8

The reaction was carried out following the procedure described in Example 1 with 0.1 ml (5.5 mmol) of water added. The butadiene conversion was found to be 79%, the product selectivities were 71% lactone (I), 2% esters (II) and 19% octatrienes, the yield of lactone being 433 mol per mol of palladium metal (averaging 24 mol per hour). This Example shows that the presence of water has increased the formation of octatrienes although the lactone selectivity is still better than in prior art processes.

EXAMPLE 9

10 ml of acetonitrile, 0.2 g (0.28 mmol) of [Pd(PPh$_3$)(p-benzoquinone)], 1 ml (8 mmol) of triethylamine, 0.1 ml (5.5 mmol) of water and 11.5 g (0.21 mol) of butadiene were reacted for 18 hours at 60° C. under 50 bar of $CO_2$ pressure as described in Example 1. The butadiene conversion was found to be 89%, the product selectivities were 70% lactone (I), 1% esters (II) and 25% octatrienes, the yield of lactone being 230 mol per mol of palladium metal (averaging 13 mol per hour).

In the absence of triethylamine, the following results were typical: butadiene conversion was found to be 49%, the product selectivities were 26% lactone (I), 18% esters (II) and 45% of octatrienes, the yield of lactone being 46 mol per mole of palladium metal (averaging 2.6 mol per hour).

EXAMPLE 10

The reaction was carried out following the procedure described in Example 1 with 0.1 g (0.13 mmol) of [Pd(PPh$_3$)$_2$(naphthoquinone)], 0.36 g (1.4 mmol) of triphenylphosphine, 1 ml (7.2 mmol) of N-ethylpiperidine, 0.1 ml (5.5 mmol) of water and 11.5 g (0.21 mol) of butadiene for 18 hours at 60° C. under 43 bar of $CO_2$ pressure. The butadiene conversion was found to be 94%, the product selectivities were 66% of lactone (I), 12% esters (II) and 22% octatrienes, the yield of lactone being 436 mol of lactone per mol of palladium metal (averaging 24 mol per hour).

In the absence of N-ethylpiperidine, the following results were typical: butadiene conversion 13%, the product selectivities were 23% lactone (I), 17% esters (II) and 47% octatrienes, the yield of lactone being 16 mol of lactone per mol of palladium metal (averaging 0.9 ml per hour).

EXAMPLE 11

[Pd{P(OMe)$_2$Ph}$_2$(p-benzoquinone)] (prepared without isolation by stirring 0.13 g (0.12 mmol) of [Pd$_2$(dibenzylidene acetone)$_3$CHCl$_3$] and 0.09 g (0.53 mmol) of P(OMe)$_2$Ph for 1 hour under nitrogen in 10 ml of acetonitrile, then adding 0.027 g (0.25 mmol) of p-benzoquinone), 1 ml (8 mmol) of triethylamine and 11.5 g (0.21 mol) of butadiene were reacted for 18 hours at 50° C. under 45 bar of $CO_2$ pressure as described in Example 1. The butadiene conversion was found to be 47%, the product selectivities were 83% of lactone (I), 11% of esters (II) and 5% of octatrienes, the yield of lactone being 170 ml per mol of palladium metal (averaging 9.5 mol per hour).

In the absence of triethylamine, the following results were typical; butadiene conversion 36%, the product selectivities were 40% lactone (I), 11% esters (II) and 42% octatrienes, the yield of lactone being 48 mol per mole of palladium (averaging 3 mol per hour).

EXAMPLE 12

0.1 g (0.34 mmol) of [Pd(pyridine)(p-benzoquinone)], 0.5 ml (4 mmol) of pyridine, 0.5 ml (4 mmol) of N-ethylpiperidine 0.1 ml (5.5 mmol) of water, 11.5 g (0.21 mol) of butadiene were reacted in 10 ml of acetonitrile for 54 hours at 50° C. under 45 bar of $CO_2$ pressure as described in Example 1. The butadiene conversion was found to be 42%, the product selectivities were 82% of lactone (I), 3% of esters (II) and 12% of octatrienes, the yield of lactone being 100 ml per mol of palladium metal (averaging 2.0 mol per hour).

In the absence of N-ethylpiperidine, the following results were typical; butadiene conversion 19%, the product selectivities were 68% lactone (I), 3% esters (II) and 25% octatrienes, the yield of lactone being 29 mol per mol of palladium metal (averaging 0.5 mol per hour).

The palladium complex used in this Example was prepared by stirring 1 g [Pd$_2$(dibenzylidene acetone)$_3$CHCl$_3$] and 4 ml of pyridine in 30 ml of tetrahydrofuran for 1 hour under a N$_2$ atmosphere, then adding 0.22 g of p-benzoquinone and stirring for a further 1 hour. The resulting precipitate was filtered, washed thoroughly with acetone and tetrahydrofuran, and then dried on a vacuum line.

EXAMPLE 13

20 ml of acetonitrile, 0.14 g (0.12 mmol) of Pd(PPh$_3$)$_4$, 0.5 ml (3.6 mmol) of N-ethylpiperidine, 0.11 g (1 mmol) of hydroquinone and 11.5 g (0.21 mol) of butadiene were reacted for 18 hours at 60° C. under 20 bar of $CO_2$ pressure as described in Example 1. The butadiene conversion was found to be 84%, the product selectivities were 91% lactone (I), 3% esters (II) and 5% octatrienes, the yield of lactone being 610 mol per mol of palladium metal (averaging 34 mol per hour).

In the absence of the N-ethylpiperidine, the following results were typical; butadiene conversion 33% and product selectivities of 74% lactone (I), 5% esters (II) and 15% octatrienes, the yield of lactone being 199 mol per mol of palladium metal (averaging 11 mol per hour).

In the absence of the hydroquinone (but in the presence of the base), the butadiene conversion was 12% the product selectivities of 91% lactone (I), 5% esters (II) and 4% octatrienes, the yield of lactone being 95 mol per mol of palladium (averaging 5 mol per hour).

What we claim is:

1. A process for the manufacture of 2-ethylidenehept-6-en-5-olide which comprises reacting in a liquid medium 1,3-butadiene with carbon dioxide in the presence of
   (a) a palladium complex catalyst which is a complex of palladium with a phosphorus (III) compound or pyridine or a substituted pyridine, and
   (b) a tertiary amine having a pKa value in the range 10 to 14.

2. A process according to claim 1 wherein the palladium complex has the structure:

wherein $R^1$ is an alkyl, cycloalkyl or aryl group and L is a ligand containing one or more unsaturated double bonds which are capable of co-ordinating with the palladium atom.

3. A process according to claim 2 wherein L is a quinone.

4. A process according to claim 1 wherein the tertiary amine is triethylamine or N-ethylpiperidine.

5. A process according to claim 1 wherein the tertiary amine is used in an amount of 10 to 100 mmol per mole of butadiene.

6. A process according to claim 1 wherein the reaction mixture contains a quinone or a hydroquinone.

7. A process according to claim 6 wherein the quinone or hydroquinone is used in an amount of 1 to 25 mmol per mole of butadiene.

8. A process according to claim 1 wherein the reaction mixture contains a phosphorus (III) compound, pyridine or a substituted pyridine.

9. A process according to claim 1 wherein the reaction mixture contains not more than 12.5 mmole of water per mole of butadiene.

10. A process according to claim 9 wherein the reaction mixture is substantially anhydrous.

11. A process according to claim 1 wherein the reaction is carried out at a pressure in the range 10 to 100 bar.

12. A process according to claim 11 wherein the reaction is carried out at a pressure in the range 10 to 50 bar.